United States Patent [19]

Celeste et al.

[11] 4,007,733
[45] Feb. 15, 1977

[54] POSTURE TRAINING DEVICE

[75] Inventors: Victor Celeste; David Charles Drum; Brian Joseph Nelson, all of Toronto, Canada

[73] Assignee: Vaxar Ltd., Toronto, Canada

[22] Filed: Feb. 23, 1976

[21] Appl. No.: 659,989

[52] U.S. Cl. .................. 128/2 S; 128/78; 340/279
[51] Int. Cl.² .......................................... A61B 5/00
[58] Field of Search ............. 128/78, 2 S; 2/44, 45; 340/279, 283

[56] References Cited

UNITED STATES PATENTS

| | | | |
|---|---|---|---|
| 330,094 | 11/1885 | Carroll et al. | 2/45 |
| 3,582,935 | 6/1971 | Verhaeghe | 340/279 |
| 3,608,541 | 9/1971 | Hall | 128/2 S |
| 3,670,320 | 6/1972 | Palmer | 340/279 |

*Primary Examiner*—John D. Yasko

[57] ABSTRACT

A posture training device having adjustable shoulder straps connected to opposite points on a waistband of clothing of a user and including signalling means to apply a sensory stimulus to the user and means to detect the relaxation of tension in the strap.

10 Claims, 4 Drawing Figures

POSTURE TRAINING DEVICE

FIELD OF THE INVENTION

This invention relates to a posture training device.

REVIEW OF THE PRIOR ART

The importance of correct posture both for health and aesthetic reasons has long been appreciated, and a number of exercises, devices and training aids have been evolved over the years, many of which possess a substantial measure of utility. However, known devices and training aids are usually only effective to correct or prevent a particular postural defect or a limited range of defects.

Thus several devices have been proposed in the form of a belt secured around the waist of a wearer and including some means effective to give a warning signal in response to an increase in tension in the belt beyond a predetermined level. The biological feedback provided by the warning signal helps to train the user not to allow his abdominal muscles to sag. Such devices have been disclosed in U.S. Pat. No. 3,582,935, Australian Pat. No. 291,096 and British Pat. No. 1,036,238. These belts are themselves inelastic except for some limited degree of local extensibility, which is sensed to actuate the warning signal.

Other devices such as those disclosed in U.S. Pat. Nos. 3,268,845; 3,520,294 and 3,820,529, have incorporated belts including elastic transducer elements for the continuous monitoring of chest or abdominal expansion; these devices are intended for quantitatively indicating the magnitude of dynamic expansions or contractions to a medical supervisor without unduly restricting a patient's movements or providing any biological feedback to the patient.

U.S. Pat. No. 3,608,541 describes a device for indicating undesirable excessive curvature of the spine by providing a warning signal. The device is complex in structure and requires the patient to wear a rather restrictive body harness, whilst only signalling those forms of undesirable spinal posture involving excessive lateral curvature.

SUMMARY OF THE INVENTION

A primary object of the present invention is to provide a method and apparatus for posture control which, whilst cheap to manufacture and easy to fit and use, is an effective aid in correcting a substantial range of postural defects.

Broadly speaking, the invention entails monitoring posture by sensing the length of an elastic strap passing from in front and to one side of a person's waist, upwardly over one shoulder, preferably on the same side as said front end of the strap, and downwardly to the rear and the other side of the person's waist. We find that the length of a strap so routed provides a good indication of the distance between the ends of the spinal column, which distance itself is determined both by the straightness of the column and its degree of compression. For reasons of body geometry, the indication is more accurate when the strap is routed over the shoulder on the same side of the wearer as the front end of the strap.

The strap is associated with a warning device so arranged that should the tension in the strap fall below a preset minimum determined by adjusting the free length of the strap, the wearer will be warned, and trained to maintain the ends of his or her spine separated by a distance proportional to the said minimum strap length. An increase in such separation can be achieved by two primary means. Firstly, the amplitude of curves in the spinal column may be reduced, and secondly the compressive forces on spinal column itself may be reduced by muscular action. The beneficial effects of such training are multiple. Excessive curvature of the spine, in any dimension, is reduced or eliminated, and the tone of the muscles used in maintaining correct spinal posture is improved. Improvement in the tone of these muscles automatically acts to decrease abdominal distension and to improve chest expansion. In certain cases at least, regular use of the device will result in an increase in the maximum extension of the spine which can be achieved, and thus to an increase in height. Reduction of spinal curvature improves posture, and decreases the local gravitational stresses placed on its components, whilst the muscle toning referred to above helps reduce the loading on the spine thus still further reducing local stresses. This stress reduction assists in the alleviation of symptoms of existing spinal damage and will help prevent such injury occurring or recurring. The device functions not only to warn the user of defective posture and thus condition him to assume a better posture, but also by reason of its elasticity provides a degree of resistance to the muscular movements required to assume that better posture, thus providing an isometric toning effect.

SHORT DESCRIPTION OF THE DRAWING

A preferred embodiment of the invention is described with reference to the accompanying drawing in which.

DESCRIPTION OF THE PREFERRED EMBODIMENT

Figure 1:
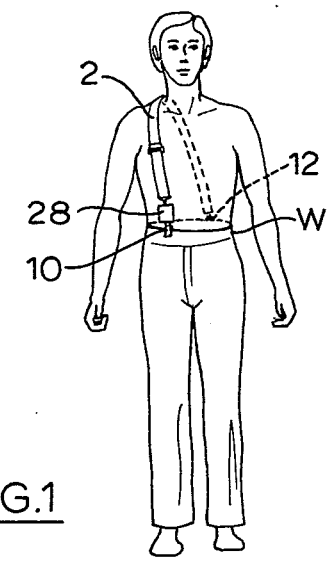
FIG. 1 is a diagram showing the device applied to a wearer.
Figure 2:
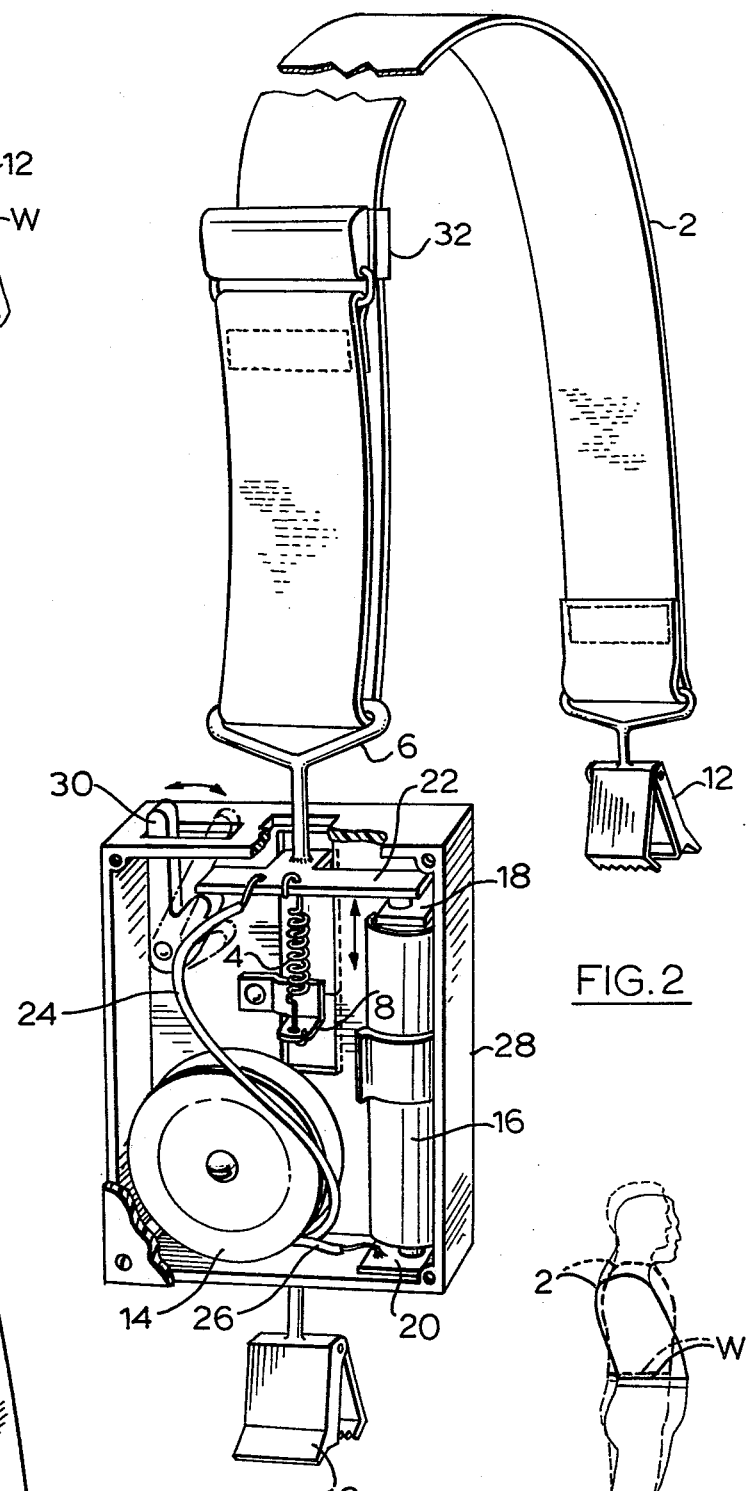
FIG. 2 shows a device in accordance with the invention.

The posture training device illustrated in FIGS. 1 and 2 of the drawings is a shoulder strap comprising a band of elasticated fabric 2 having a substantial capability for elastic extension beyond its normal unstressed length, a strainable element in the form of a spring 4, connected at one end to one end of the shoulder strap through a shackle 6 and at the other end to an anchorage 8, releasable means 10 and 12 in the form of clips for securing the anchorage 8 and the other end of the shoulder strap to diagonally opposite points on a waistband of clothing worn by the user, and a box 28 connecting the anchorage 8 and the clip 10 and enclosing a buzzer 14, a battery 16 (by means of clips 18 and 20), a switch element 22 which establishes the connection between the spring 4 and the shackle 6, and wires 24 and 26 connecting the switch element 22 and the clip 20 to the buzzer.

By 'waistband' we mean either a waistband of items of clothing such as trousers, pants, skirts, dresses or any articles of clothing capable of maintaining a reasonably well defined position relative to the pelvis of the wearer, or a belt having a similarly capability either on its own or when used to support a nether garment. By diagonally opposite points on a waistband we mean points one of which is to the front and one side of the body and the other of which is to the rear and other side of the body, as shown in FIG. 1.

Figure 4:
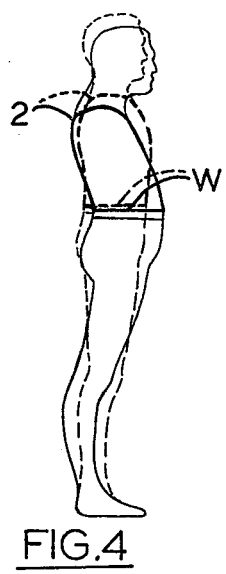
FIG. 4 is a diagram illustrating the operation of the device.

In use, one end of the strap is connected to the waistband at the front and to one side of the waistband, in a similar position to a front strap of a conventional pair of suspenders. The releasable means 10 used for this purpose may be a clip with serrated jaws as shown, or any other suitable fastening means. It is believed however that a clip with spring loaded or suitably clampable jaws, or a fastening comprising a patch of hooked pile fabric such as that sold under the trade mark VELCRO is likely to be the most versatile in permitting attachment of the clips 10 and 12 to different types of waistband W. The band 2 is passed over the shoulder on the same side as the means 10 and the releasable means 12 is attached to the waistband at the rear of the body but on the other side. In the embodiment shown the box 28 is located at the front end of the strap adjacent the clip 10 with a switch actuating lever 30 projecting upwardly. These locations may be varied provided that the clip and switch are readily accessible to the user. The length of the strap is adjusted by means of conventional sliding buckles 32 at either or both ends of the band 2 so that a predetermined degree of upward lift of the user's shoulders relative to his or her waist W, corresponding to minimum degree of spinal extension which is to be maintained, results in a degree of extension of the strap from its unstressed length. This is illustrated in FIG. 4 which illustrates a typically poor posture in full lines, and in broken lines a good posture resulting from extension of the spine as by use of the device of the invention. Such extension in turn entails the presence of a certain minimum tension in the strap which is sufficient to cause extension of the spring 4 so that the switch element 22 is held away from the clip 18. Thus so long as the user's spine is sufficiently extended, a circuit cannot be completed between the battery 16 and the buzzer 14. However, if the switch actuating lever is in the position shown in broken lines, any relaxation of tension in the strap sufficient to permit the spring 4 to contract will result in a circuit being completed between the battery and the buzzer, thus warning the user that the required minimum degree of spinal extension needed to extend the strap is not being maintained. Movement of the switch actuating lever 30 to the position shown in full lines prevents the switch member from contacting the clip 18, thus enabling the device to be fitted or removed and stored without the buzzer sounding. The box 28 of course includes a cover (not shown).

A number of variations are possible in the above design. The buzzer 14 could be replaced by other means providing a sensible stimulus to the user, such as a light, or an induction coil having a secondary winding attached to skin contacting electrodes so as to administer harmless electric shocks to the user. Moreover the buzzer or other warning means could be separate from the remainder of the device and connected thereto by flexible wires or a radio or ultrasonic link. Instead of an electrically operated buzzer, a clockwork operated buzzer or bell could be employed, the electrical switch member being replaced by a mechanical switch member movable into and out of a position in which it blocks operation of a spring driven escapement. The spring 4 and its anchorages could be arranged so that a compression spring could be employed instead of a tension spring, or the switch element itself could be formed by a resilient contact blade, thus eliminating the spring. Indeed, all that is required is a resiliently strainable element which acts to disable the warning means so long as a certain minimum strain is maintained. The resiliently strainable element could be a portion of the elastic strap: for example, in the embodiment shown in FIG. 2, the band 2 could be continued through a clip 32 replacing the shackle 6 and a clip 34, the spring 4 being eliminated. The box 28 may then be situated at an intermediate point on the band 2 instead of at its front end.

The invention could also be embodied in a pair of suspenders, the band 2 being provided by a front strap of the suspenders with the box 28 and its associated parts incorporated therein or attached thereto. In this case, if the straps at the rear of the pair of suspenders were arranged in a Y rather than an X formation, the rear clip or clips would be more or less central: however this arrangement is mechanically equivalent to the X formation in which the rear clips would be attached to the waistband on opposite sides of the body from their front ends.

It is also contemplated that a device incorporating a warning device could be provided for attachment by clips to spaced points on one of the front straps of a pair of suspenders, each of said clips being attached to relatively movable parts of a switch mechanism controlling a warning device so that said switch is operative to activate said warning device when said strap is substantially relaxed and to deactivate said warning device when said strap is extended.

Figure 3:
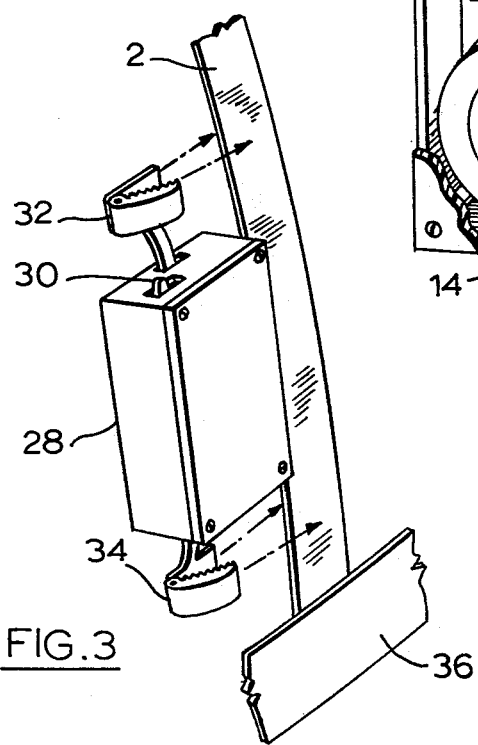
FIG. 3 shows a modified form of the device.

In another variant, the ends of the shoulder strap could be connected to a belt 36 (see FIG. 3) forming part of the device and adapted to be secured around the user in a defined position relative to his or her pelvis, the necessity for relying on a separate waistband.

In any variant of the device, however, two strainable elements are required in the strap: a first element in the form of an elasticated band or a part thereof which is capable of a substantial degree of elastic elongation, and a second element, which may also be part of the elasticated band, which is strained dependent on the tension in the first element and actuates the warning device. The elasticity of the first element is necessary to allow free body movement without disrupting the device and so as to provide the isometric toning effect referred to above.

Adjustability of the free length of the strap is usually necessary so as to accommodate the device to the user, and to adjust the device for progressively increasing degrees of spinal elongation as training proceeds.

What we claim is:

1. A posture training device comprising a shoulder strap whose length is adjustable and resiliently extensible, means at each end of the shoulder strap for releasably connecting it to substantially diagonally opposite points on a waistband of clothing of a user, a device providing a warning signal sensible by the user, and means connected into the strap and to said signalling device to disable the latter in response to maintenance of a predetermined minimum tension in the strap.

2. A posture training device comprising a shoulder strap having substantial elastic extensibility and an adjustable free length, means for establishing releasable connections between the ends of said strap and diagonally opposite points on a waistband worn by a user, a switch means comprising an element connected between two relatively movable points on said strap, said element being resiliently strainable in response to tension in said strap, and a warning device providing a stimulus sensible to the user, said warning device being operatively linked to said switch for activation on relaxation of said strainable element and deactivation on straining of said strainable element.

3. A posture training device according to claim 2 wherein the strainable element is a spring.

4. A posture training device according to claim 2 wherein the strainable element is a minor portion of a strip of elasticated fabric of which the major portion forms a major portion of the extensible strap.

5. A posture training device according to claim 2 wherein the warning device is electrically operated and the switch means comprises relatively movable contacts whose relative position is controlled by the strainable element so that they are in contact when said element is relaxed and apart when it is strained, said switch means forming part of a circuit connecting said warning device to a battery.

6. A posture training device according to claim 5, wherein said warning device is a buzzer.

7. A posture training device comprising at least one band of elastic material, two clips for releasable attachment to diagonally opposite points on a waistband, and a switchable warning device comprising a box having two separate attachment points joined by a resilient element, said at least one band, said attachment points on said box and said end clips being joined to form a continuous shoulder strap with said clips at each end, and said warning device further comprising means providing a signal sensible by a wearer of the device, a power source for said signal providing means, and switch means operative on movement apart of said external attachment means against the resilience of said resilient element to interrupt the transmission of power from said power source to said signal providing means.

8. A device according to claim 7 wherein said signal providing means is electrically operated, said power source is a battery, and said switch means interrupts an electrical circuit connecting said battery to said signal providing means.

9. A posture training device comprising a belt securable around a user in a defined position relative to the user's pelvis, a shoulder strap passing from the belt to the front and one side of the user, over the user's shoulder on said one side to the belt to the rear and the other side of the user, the shoulder strap including a band of elasticated material and being adjustable in length so that the assumption by the user of a posture involving a predetermined degree of extension of the spine will tension the strap, means incorporated in the strap to detect the relaxation of tension in the strap, and means actuated by said detection means to apply a sensory stimulus to the user.

10. A method of monitoring the posture of a human subject, comprising linking a first point on a waistband worn by the subject in a defined relation to the user's pelvis, said first point being to the front and one side of the user, to a second point on the waistband to the rear and other side of the subject by means of an elastically extensible strap passing over the shoulder of the subject on said one side so that the tension in the strap exceeds a predetermined minimum as long as a desired posture is maintained, and applying a sensory stimulus to the subject in response to the tension in the strap falling below said predetermined minimum.

* * * * *